(12) United States Patent
Seo et al.

(10) Patent No.: US 7,518,007 B2
(45) Date of Patent: Apr. 14, 2009

(54) GE PRECURSOR, GST THIN LAYER FORMED USING THE SAME, PHASE-CHANGE MEMORY DEVICE INCLUDING THE GST THIN LAYER, AND METHOD OF MANUFACTURING THE GST THIN LAYER

(75) Inventors: Bum-seok Seo, Seoul (KR); Jung-hyun Lee, Yongin-si (KR)

(73) Assignee: Samsung Electronics Co., Ltd., Suwon-Si, Gyeonggi-Do (KR)

( * ) Notice: Subject to any disclaimer, the term of this patent is extended or adjusted under 35 U.S.C. 154(b) by 255 days.

(21) Appl. No.: 11/253,693

(22) Filed: Oct. 20, 2005

(65) Prior Publication Data

US 2006/0138393 A1 Jun. 29, 2006

(30) Foreign Application Priority Data

Dec. 27, 2004 (KR) ............... 10-2004-0112906

(51) Int. Cl.
C07F 7/08 (2006.01)
C07F 7/00 (2006.01)
C23C 16/00 (2006.01)

(52) U.S. Cl. ................. 556/12; 556/9; 556/81
(58) Field of Classification Search ............ 556/9, 556/12, 81
See application file for complete search history.

(56) References Cited

U.S. PATENT DOCUMENTS 6,197,983 B1   3/2001  Litz et al.
6,969,539 B2 * 11/2005 Gordon et al. ......... 427/255.29

FOREIGN PATENT DOCUMENTS

| JP | 2004-131485 | 4/2004 |
| KR | 10-2001-0098415 A | 11/2001 |
| KR | 10-2003-0084126 A | 11/2003 |
| KR | 10-2004-0038023 A | 5/2004 |
| KR | 10-2004-0076225 | 8/2004 |
| WO | 02/27063 A2 | 4/2002 |

OTHER PUBLICATIONS

Korean Office Action (with English language translation) dated Apr. 25, 2006.
European Search Report (in English) issued in corresponding European Application No. 05256447.3 on Sep. 27, 2006, Munich, Germany.
Liu, Bo, et al., "*Nitrogen-implanted $Ge_2Sb_2Te_5$ film used as multilevel storage media for phase change random access memory*", Semiconductor Science and Technology, Jun. 1, 2004, vol. 19, No. 6, Institute of Physics Publishing, Bristol, GB.

* cited by examiner

*Primary Examiner*—Porfirio Nazario Gonzalez
(74) *Attorney, Agent, or Firm*—Buchanan Ingersoll & Rooney PC

(57) ABSTRACT

Provided are a Ge precursor for low temperature deposition containing Ge, N, and Si, a GST thin layer doped with N and Si formed using the same, a memory device including the GST thin layer doped with N and Si, and a method of manufacturing the GST thin layer. The Ge precursor for low temperature deposition contains N and Si such that the temperature at which the Ge precursor is deposited to form a thin layer, particularly, the GST thin layer doped with N and Si, can be low. In addition, during the low temperature deposition, $H_2$ plasma can be used. The GST phase-change layer doped with N and Si formed from the Ge precursor for low temperature deposition has a low reset current. Therefore, a memory device including the GST phase-change layer doped with N and Si can be highly integrated, have a high capacity, and can be operated at a high speed.

9 Claims, 6 Drawing Sheets

CONVENTIONAL Ge precursor
; Ge(nBu)

330 Å

Ge precursor
; Ge-N-Si-R

GE PRECURSOR, GST THIN LAYER FORMED USING THE SAME, PHASE-CHANGE MEMORY DEVICE INCLUDING THE GST THIN LAYER, AND METHOD OF MANUFACTURING THE GST THIN LAYER

BACKGROUND OF THE DISCLOSURE

This application claims the benefit of Korean Patent Application No. 10-2004-0112906, filed on Dec. 27, 2004, in the Korean Intellectual Property Office, the disclosure of which is incorporated herein in its entirety by reference.

1. Field of the Disclosure

The present disclosure relates to a Ge precursor, a GST thin layer formed using the same, and a method of manufacturing the GST thin layer, and more particularly, to a Ge precursor for low temperature deposition containing Ge, N, and Si, a GST thin layer formed at a low temperature using the Ge precursor, a phase-change memory device including the GST thin layer, and a method of manufacturing the GST thin layer.

2. Description of the Related Art

Phase-change materials exist in a crystalline state or an amorphous state according to temperature. A phase-change material has a lower resistance and a more ordered atomic arrangement in a crystalline state than in an amorphous state. A phase-change material can be reversibly transformed from the crystalline state to the amorphous state. In other words, a phase-change material can transform from the crystalline state to the amorphous state, and from the amorphous state to the crystalline state. Such characteristics, that is, reversible phase change and different resistances of different states, are used in phase-change random access memory (PRAM) devices.

Typically, PRAM includes a phase-change layer electrically connected to a source region or drain region of a transistor via a contact plug. PRAM operates based on the change in resistance resulting from the change of the crystalline structure of a phase-change layer. FIG. 1 is a sectional view of a conventional PRAM.

Referring to FIG. 1, a first impurity region 11a and a second impurity region 11b are formed in a semiconductor substrate 10. A gate insulating layer 12 contacts the first impurity region 11a and the second impurity region 11b. A gate electrode layer 13 is formed on the gate insulating layer 12. The first impurity region 11a refers to a source, and the second impurity region 11b refers to a drain.

An insulating layer 15 is formed on the first impurity region 11a, the gate electrode layer 13, and the second impurity region 11b. A contact plug 14 penetrates through the insulating layer 15 and contacts the second impurity region 11b. A lower electrode 16 is formed on the contact plug 14, and a phase-change layer 17 and an upper electrode 18 are sequentially formed on the lower electrode 16.

A method of storing data in the PRAM will now be described. When a current is supplied through the second impurity region 11b and the lower electrode 16, joule heating occurs at an interface region between the lower electrode 16 and the phase-change layer 17 such that the crystal structure of the phase change layer 17 is changed. In other words, the crystal structure of the phase-change layer 17 can be changed by properly changing the applied current. Such a phase change between a crystalline phase and an amorphous phase leads to a change in resistance, which enables identification of stored binary data values.

Up to now, various phase-change materials available for use in memory devices have been developed, such as a GST (GeSbTe) alloy. For example, Korean Patent No. 2004-0100499 discloses a semiconductor memory device including a chalcogenide material layer.

In order to improve the performance of memory devices, power consumption must be decreased. However, a PRAM including a conventional phase-change GST has a high reset current, which is a current needed to change the state of a phase-change material from a crystalline state to an amorphous state.

FIG. 2 is a graph illustrating a heating temperature for reset/set programming of a memory device including a $Ge_2Sb_2Te_5$ phase-change layer.

Referring to FIG. 2, when setting programming, i.e., the transition from an amorphous state to a crystalline state can be realized at a temperature below the melting point (Tm) of GST layer for a predetermined time. On the other hand, when reset programming, i.e., the transition from the crystalline state to the amorphous state can be realized by heating to the melting point (Tm) of GST layer and then quenching. In order to increase the temperature to Tm, a large amount of a current must be supplied, which is undesirable for a highly integrated memory device.

SUMMARY OF THE DISCLOSURE

The present invention may provide a Ge precursor which can be deposited at a low temperature; a GST thin layer that is formed using the Ge precursor and consumes little current for reset and set programming, a phase-change memory device including the GST thin layer, and a method of manufacturing the GST thin layer.

According to an aspect of the present invention, there may be provided a Ge precursor for low temperature deposition containing Ge, N, and Si.

According to another aspect of the present invention, there may be provided a Ge—Sb—Te(GST) thin layer doped with N and Si formed using a Ge precursor for low temperature deposition containing Ge, N, and Sl; an Sb precursor; and a Te precursor.

According to still another aspect of the present invention, there may be provided a method of manufacturing a GST thin layer doped with N and Si comprising depositing a Ge precursor for low temperature deposition, a Sb precursor, and a Te precursor at a deposition temperature equal to or less than 350°.

According to yet another aspect of the present invention, there is provided a phase-change memory device including: a semiconductor substrate; a first impurity region and a second impurity region formed in the semiconductor substrate; a gate structure formed on a channel region interposed between the first impurity region and the second impurity region; a lower electrode connected to the second impurity region; a GST phase-change layer doped with N and Si formed on the lower electrode; and an upper electrode formed on the GST phase-change layer. The GST phase-change layer doped with N and Si is formed from a Ge precursor that can be deposited at a low temperature, a Sb precursor, and a Te precursor.

The Ge precursor according to the present invention contains N and Si such that a GST thin layer with a uniform thickness suitable for various devices can be formed using the Ge precursor at a low temperature. The GST thin layer formed using the Ge precursor is doped with N and Si such that a reset current applied to change a crystal structure of the GST thin layer can be low. As a result, a phase-change device including the GST thin layer may have good performance characteristics.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF EXEMPLARY EMBODIMENTS

Figure 1:
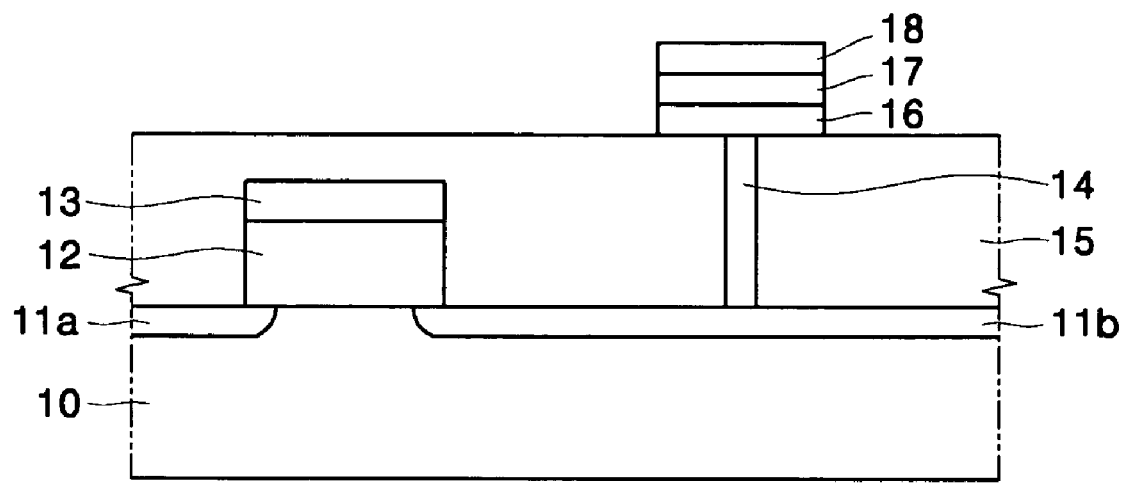
FIG. 1 is a sectional view of a conventional phase-change random access memory (PRAM)
Figure 2:
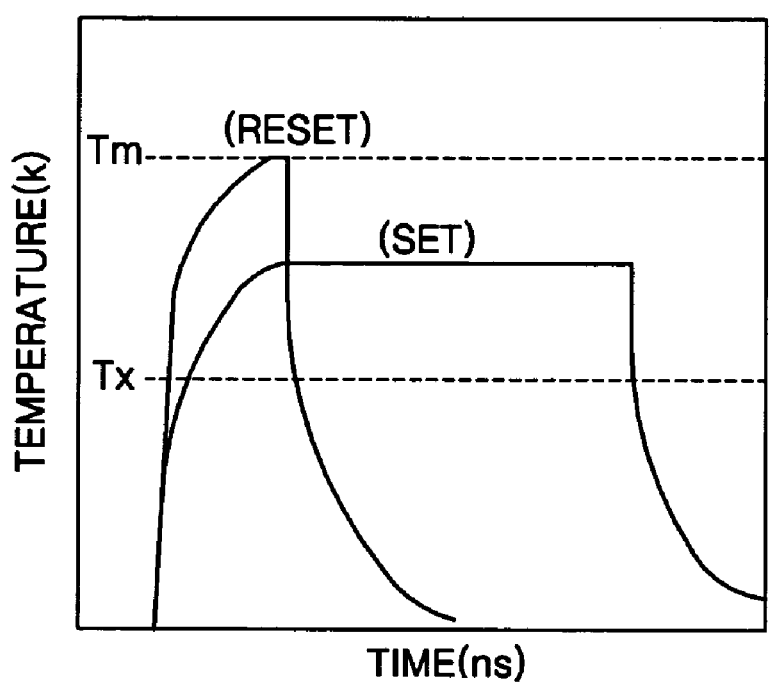
FIG. 2 is graph illustrating a heating temperature for reset/set programming of a memory device including a $Ge_2Sb_2Te_5$ phase-change layer.

A Ge precursor for low temperature deposition according to an embodiment of the present invention contains Ge, N, and Si. In the present specification, the term "for low temperature deposition" indicates that the Ge precursor according to the present invention can be deposited to a predetermined thickness at a lower temperature than a conventional Ge precursor, such as a Ge precursor containing N but not Si, a Ge precursor containing Si but not N, or a Ge precursor that does not contain either N or Si. In this case, "the low temperature" is equal to or less than 350°, for example.

The Ge precursor that can be deposited at a low temperature may be represented by;

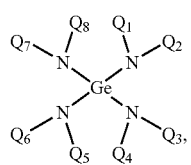

(1)

where $Q_1$, $Q_2$, $Q_3$, $Q_4$, $Q_5$, $Q_6$, $Q_7$, and $Q_8$ are each independently, H, a $C_{1-5}$ alkyl group, or $SiR_1R_2R_3$ where $R_1$, $R_2$ and $R_3$ are each independently, H or a $C_{1-5}$ alkyl group. At least one of, preferably three of, and most preferably all of $Q_1$, $Q_2$, $Q_3$, $Q_4$, $Q_5$, $Q_6$, $Q_7$ and $Q_8$ is $SiR_1R_2R_3$.

In an exemplary embodiment of the present invention, the Ge precursor for low temperature deposition may be represented by formula 2, where all of $Q_1$, $Q_2$, $Q_3$, $Q_4$, $Q_5$, $Q_6$, $Q_7$ and $Q_8$ are $SiR_1R_2R_3$.

(2), where $R_1$, $R_2$ and $R_3$ are each independently H or a $C_{1-5}$ alkyl group. In this case, the $C_{1-5}$ alkyl group may be a methyl group, an ethyl group, a propyl group, a butyl group, or a pentyl group.

In formula 2, it is preferred that all of $R_1$, $R_2$ and $R_3$ are a methyl group. In another embodiment of the present invention, the Ge precursor may be represented by formula 3.

(3)

The Ge precursor for low temperature deposition can be manufactured using various methods. An exemplary method will now be described.

First, an aminosilane-based compound having a N—Si bond is reacted with an alkali metal-containing material, thus producing an aminosilane-based compound substituted with at least an alkali metal. The aminosilane-based compound having a N—Si bond may be hexamethyldisilazane, heptamethyldisilazane, or the like, but is not limited thereto. The alkali metal-containing material may be nBu—Li, or the like, but is not limited thereto. The reaction between the aminosilane having a N—Si bond and the alkali metal-containing material may occur in an organic solvent such as hexane or the like.

Then, the aminosilane-based compound substituted with at least an alkali metal is stoichiometrically reacted with a Ge-containing compound substituted with a halogen atom to obtain a Ge precursor for low temperature deposition having a Ge—N bond and a N—Si bond. Such a Ge-containing compound substituted with a halogen atom may be $GeCl_4$, $GeF_4$, or the like, but is not limited thereto. The reaction between the aminosilane-based compound substituted with at least an alkali metal and the Ge-containing compound substituted with a halogen atom can occur in a solvent such as THF, or the like. The resulting Ge precursor is purified using various purification methods and separated using various separating methods, thus forming a deposition source for forming a thin layer.

Hereinbefore, although an exemplary method of manufacturing the Ge precursor is described, the Ge precursor can be manufactured using other methods.

The present invention discloses a Ge—Sb—Te thin layer (GST) doped with N and Si produced from the Ga precursor for low temperature deposition, an Sb precursor, and a Te precursor.

In the specification, "a GST thin layer doped with N and Si" refers to a thin layer composed of a Ge—Sb—Te based material doped with N and Si, and "a GST phase-change layer doped with N and Si" refers to a phase-change layer composed of a Ge—Sb—Te based material doped with N and Si. In addition, the term "produced from" implies that the GST thin layer can be manufactured using various methods in which the Ge precursor for low temperature deposition, the Sb precursor, and the Te precursor are used as starting materials.

The Ge precursor for low temperature deposition is the same as described above. Each of the Sb precursor and the Te precursor must be a material that can be used with the Ge precursor for low temperature deposition. The Sb precursor may be a Sb-containing compound, such as $Sb(CH_3)_3$, $Sb[N(CH_3)_2]_3$, $Sb[N(Si(CH_3)_3)_2]_3$, or the like, but is not limited thereto. The Te precursor may be a Te-containing compound, such as $Te[CH(CH_3)_2]$, and the like, but is not limited thereto.

In the GST thin layer doped with N and Si, the composition ratio of Ge, Sb, and Tb may vary. For example, the GST thin layer doped with N and Si may include a GeSb$_2$Te$_5$ layer doped with N and Si.

Figure 3:
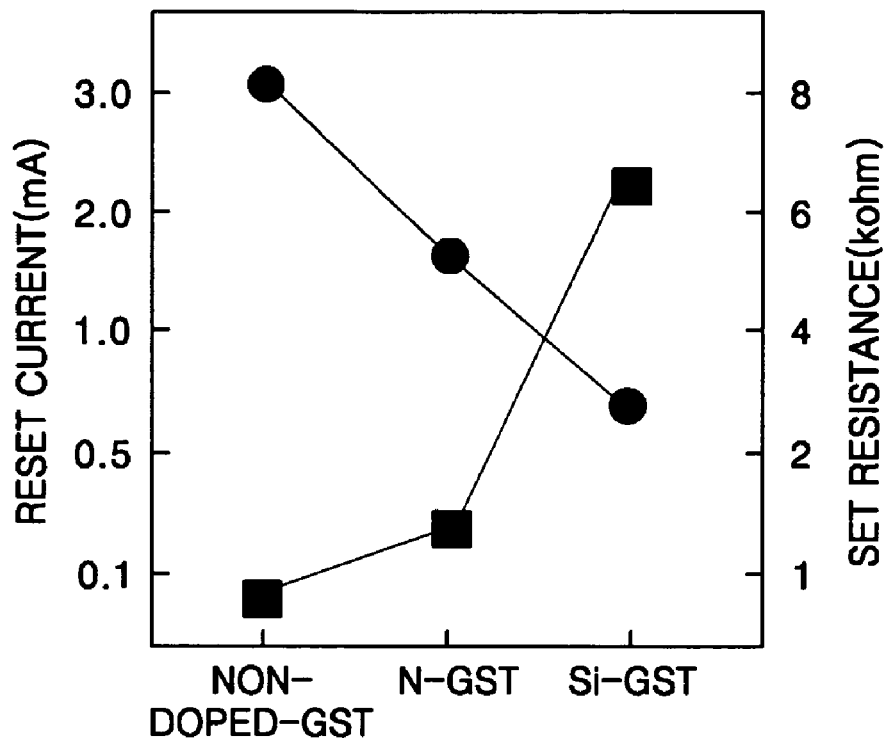
FIG. 3 illustrates the reset current (mA) and set resistance (kohm) for various materials composing a phase-change layer.

A crystalline GST thin layer doped with N and Si can be changed to an amorphous GST thin layer using a low reset current, and a high set resistance. FIG. 3 illustrates the reset current (mA) and set resistance (kohm) for various materials forming a phase-change layer. In order to measure reset currents and set resistances, TiN was used to form upper and lower electrodes and a phase-change layer was disposed between the upper and lower electrodes, thus forming a PRAM. In this instance, a non-doped GST (Ge$_2$Sb$_2$Te$_5$) layer, a GST layer doped with N, and a GST doped with Si were respectively used as the phase-change layer. Then, currents required for the transition from a crystalline state to an amorphous state, that is, reset currents, and set resistances of the PRAMs were measured.

Referring to FIG. 3, the non-doped GST layer had a reset current of 3 mA and a set resistance of about 0.8 kohm, the GST doped with N had a reset current of about 1.5 mA and a set resistance of about 1.5 kohm, and the GST doped with Si had a reset current of about 0.7 mA and a set resistance of 6.2 kohm. That is, when the GST was doped with N or Si, the phase-change characteristics of the GST phase-change layer were maintained, the reset current decreased substantially, and the set resistance increased. In other words, the doping of the GST phase-change layer with Si or N contributes to a transition with ease from the crystalline state to the amorphous state at a low temperature.

A method of manufacturing the GST thin layer doped with N and Si according to an embodiment of the present invention includes depositing the Ge precursor for low temperature deposition, the Sb precursor, and the Te precursor at a deposition temperature equal to or less than about 350° C. The Ge precursor for low temperature deposition, the Sb precursor, and the Te precursor are as described above.

The temperature at which the GST thin layer doped with N and Si is formed may be much lower than the temperature at which a conventional Ge precursor is deposited. In detail, the GST thin layer doped with N and Si may be formed at a temperature equal to or less than about 350° C. The lower limit of the deposition temperature may be determined by the thickness of a thin layer to be formed and a Te/(Ge+Sb) cation ratio. For example, when the GST thin layer doped with N and Si is formed to a thickness of about 330 Å, the deposition temperature may be equal to or greater than about 200° C. In the method of manufacturing the GST thin layer doped with N and Si according to an embodiment of the present invention, the deposition temperature may be equal to or less than about 350° C., preferably in the range of about 200° C. to 350° C., and more preferably about 250° C.

Such a deposition temperature is very different from the conventional deposition temperature. That is, when a GST thin layer is formed using a conventional Ge precursor, the deposition temperature suitable for forming a thin layer with a desired predetermined thickness is greater than about 500° C. (the details will be provided later in the specification). In addition, when the Ge precursor and the Te precursor are deposited together at a temperature equal to or greater than about 350° C., the Te component in the Te precursor can volatilise, which is not desirable for obtaining a desired Te/(Ge+Sb) cation ratio in the GST thin layer. In order to prevent the volatilisation of Te component, the deposition temperature can be decreased, but when a conventional Ge precursor is deposited at a temperature equal to or less than about 350° C., a thin layer with proper characteristics cannot be achieved.

On the other hand, when the Ge precursor for low temperature deposition according to an embodiment of the present invention is deposited with the Sb precursor and the Te precursor at a low temperature, in particular, at a temperature equal to or less than about 350° C., GST thin layer with a uniform thickness can be formed. At this time, the Te component does not volatilise. Thus, a thin layer with a desired Te/(Ge+Sb) cation ratio can be formed with ease without loss of starting materials. Further, since the Ge precursor for low temperature deposition according to an embodiment of the present invention as a deposition source contains N and Si, there is no need for additional N and Si doping processes in order to obtain the GST thin layer doped with N and Si.

The GST thin layer doped with N and Si can be deposited by chemical vapor deposition (CVD) or atomic layer deposition (ALD), or the like, but is not limited thereto. The CVD and ALD can be performed using various known methods. The ALD may include plasma enhanced atomic layer deposition (PEALD). The use of CVD or ALD can be easily understood with reference to Korean Patent Nos. 2003-0079181, 2001-0033532, and 2002-0084616. The descriptions of CVD and ALD in these patents are incorporated herein by reference.

In particular, the method of manufacturing the GST thin layer doped with N and Si according to an embodiment of the present invention may include PEALD, preferably, PEALD using hydrogen plasma. The PEALD using hydrogen plasma may apply a decomposition reaction using H$_2$/NH$_3$ plasma.

The GST thin layer doped with N and Si formed from the Ge precursor for low temperature deposition according to an embodiment of the present invention may have characteristics of a phase-change layer such that the GST thin layer doped with N and Si can be variously used. For example, the GST thin layer doped with N and Si can be used as a phase-change layer of a phase-change memory device.

A phase-change memory device including a phase-change layer containing N and Si formed from a Ge precursor for low temperature deposition, and a method of manufacturing the device will now be described.

Figure 4:
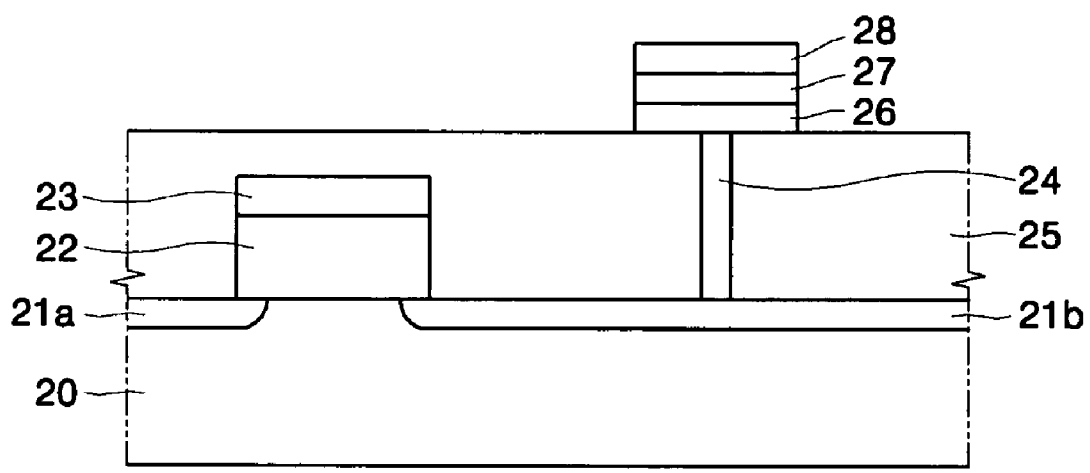
FIG. 4 is a sectional view of a phase-change memory device including a GST thin layer doped with N and Si according to an embodiment of the present invention.

FIG. 4 is a sectional view of a phase-change memory device according to an embodiment of the present invention.

Referring to FIG. 4, a first impurity region 21a and a second impurity region 21b are formed by doping a semiconductor substrate 20 with a N-type dopant or a p-type dopant. The polarities of the first and second impurity regions 21a and 21b are opposite to the polarity of the semiconductor substrate 20. A channel region is formed between the first impurity region 21a and the second impurity region 21b in the semiconductor substrate 20. A gate insulating layer 22 and a gate electrode layer 23 are sequentially formed on the channel region.

An insulating layer 25 is formed on the first impurity region 21a, the gate electrode layer 23, and the second impurity region 21b. The insulating layer 25 has a contact hole (not shown) exposing the second impurity region 21b. A conducting plug 24 is formed in the contact hole. A lower electrode 26, a phase-change layer 27, and an upper electrode 28 are sequentially formed on the conducting plug 24. The phase-change layer 27 may be the GST thin layer containing Si and N. The GST may be GeSb$_2$Te$_5$.

An underlying structure of the phase-change layer 27 can be easily formed using conventional semiconductor manufacturing processes. In FIG. 4, the lower electrode 26 and the conducting plug 24 may be integrally formed. That is, the phase-change layer 27 may be directly formed on the conductive plug 24 so that the conductive plug 24 serves as the lower electrode 26. In this structure, when a current is directly supplied to the conducting plug 24, joule heating occurs. At this time, the conducting plug 24 is used as a heating plug.

A method of manufacturing a phase-change memory device according to an embodiment of the present invention will now be described.

First, a gate insulating material and a gate electrode material are sequentially coated on a semiconductor substrate 20. Then, side portions of the gate insulating material and the electrode material are removed to form a gate insulating layer 22 and a gate electrode layer 23. The surface of the semiconductor substrate 20 exposed by the gate insulating layer 22 and the gate electrode layer 23 is doped with impurities to form a first impurity region 21a and a second impurity region 21b. Then, an insulating layer 25 is formed on the first impurity region 21a, the gate electrode layer 23, and the second impurity region 21b. A contact hole exposing the second impurity region 21a is formed in the insulating layer 25. The contact hole is filled with a conducting material, thus forming a conducting plug 24.

Optionally, a conducting material may be coated on the conducting plug 24 to form a lower electrode 26. In this case, the conducting material may be a noble metal, a metal nitride such as TiN, or the like. Conventionally, when the phase-change layer 27 is formed on the conducting plug 24 or the lower electrode 26, a sputtering using a Ge—Sb—Te material as a target is often used.

However, in the present invention, a Ge precursor for low temperature deposition containing Ge, N, and Si, the Sb precursor, and the Te precursor react together on a substrate in a reaction chamber. As a result, the GST phase-change layer containing N and Si can be produced. At this time, the deposition temperature may be equal to or less than about 350° C., and preferably in the range of about 200° C. to about 350° C. Then, the same conductive material as the lower electrode 26 is coated on the phase-change layer 27 to form an upper electrode 28. As a result, a phase-change memory device according to the present embodiment is completely formed.

Hereinafter, the present invention will be described in detail while describing exemplary embodiments of the invention with reference to the attached drawings. Like reference numerals in the drawings denote like elements.

EMBODIMENTS

Embodiment 1

Reaction Scheme 1

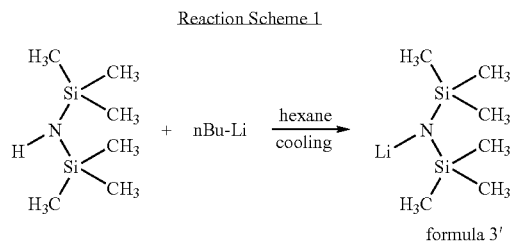

formula 3'

In Reaction Scheme 1, a solution of 0.1 moles of hexamethyldisilazane in 1000 ml of hexane and 0.2 mole of nBu—Li were mixed at room pressure and −78°, and then reacted for 4 hours at room temperature. As a result, the compound of formula 3' was produced.

Reaction Scheme 2

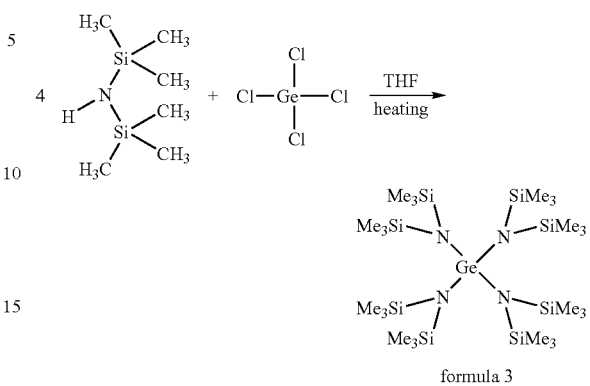

formula 3

Figure 5A:
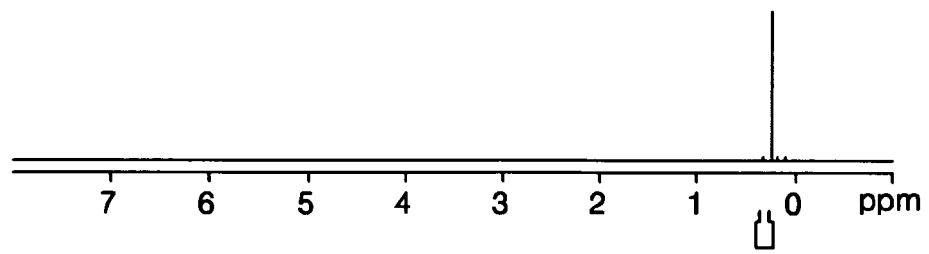
FIGS. 5A and 5B illustrate $^1$H-NMR analysis results and $^{13}$C-NMR analysis results of a Ge precursor for low temperature deposition according to an embodiment of the present invention, respectively.
Figure 5B:
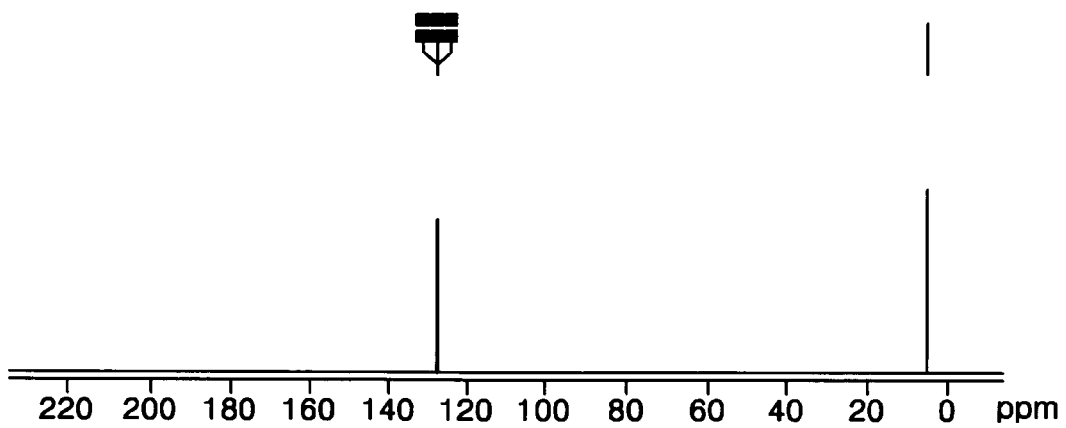

In Reaction Scheme 2, 0.5 mole of the compound of formula 3' and 0.1 mole of $GeCl_4$ were mixed in 1000 ml of THF, reacted at 150° C. for 8 hours, and dried in a vacuum at room temperature. The resultant product was purified by fractional distillation at 0.1 torr and 60° C. to obtain 38 g of the compound of formula 3, that is, $Ge[N(Si(CH_3)_3)_2]_4$. Then, the compound of formula 3 was identified by $^1$H-NMR and $^{13}$C-NMR, all of which were performed at 25° C. with $C_6D_6$. The results are shown in FIGS. 5A and 5B, respectively. Referring to FIGS. 5a and 5b, the presence of a Ge—N bond and a N—Si bond in the compound of formula 3 can be confirmed. The compound of formula 3 refers to a Ge precursor 1.

COMPARATIVE EXAMPLE A $Ge(CH_3)_4$ obtained from Aldrich Co. will be referred as Ge precursor A.

COMPARATIVE EXAMPLE B $Ge[N(CH_3)_2]_4$ obtained from Aldrich Co. will be referred as Ge precursor B.

MEASUREMENT EXAMPLE 1

Thermal Decomposition Characteristics

Figure 6:
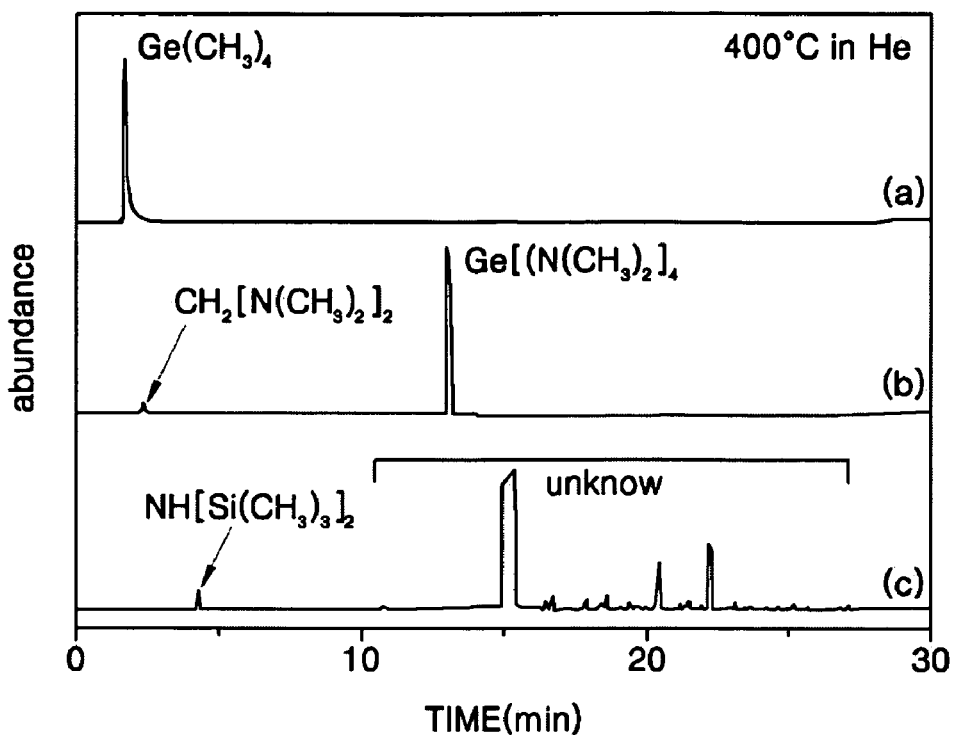
FIG. 6 illustrates thermal decomposition properties of a Ge precursor for low temperature deposition according to an embodiment of the present invention and conventional Ge precursors.

The thermal decomposition characteristics of Ge precursors A, B, and 1 were measured. The results are shown in FIG. 6. The thermal decomposition was performed at 400° C. in a He atmosphere in an injection chamber system. The results were measured using gas chromatography. In FIG. 6, (a) illustrates a peak of $Ge(CH_3)_4$ that is the Ge precursor A, (b) illustrates a peak of $Ge[N(CH_3)_2]_4$ that is the Ge precursor B, and (c) illustrates a peak of $Ge[N(Si(CH_3)_3)_2]_4$ that is the Ge precursor 1. Comparing (c) to (a) and (b), it was confirmed that the Ge precursor 1 according to an embodiment of the present invention decomposed in a shorter time than Ge precursors A and B. That is, since the rate of thermal decomposition of Ge precursor 1 according to an embodiment of the preset invention is higher than those of the conventional Ge precursors A and B, the Ge precursor 1 is more suitable for CVD or ALD.

MEASUREMENT EXAMPLE 2

Layer Forming Ability at a Low Temperature

The layer forming ability was measured using the Ge precursor A, and the Ge precursor 1. At this time, ALD was used.

Figure 7A:
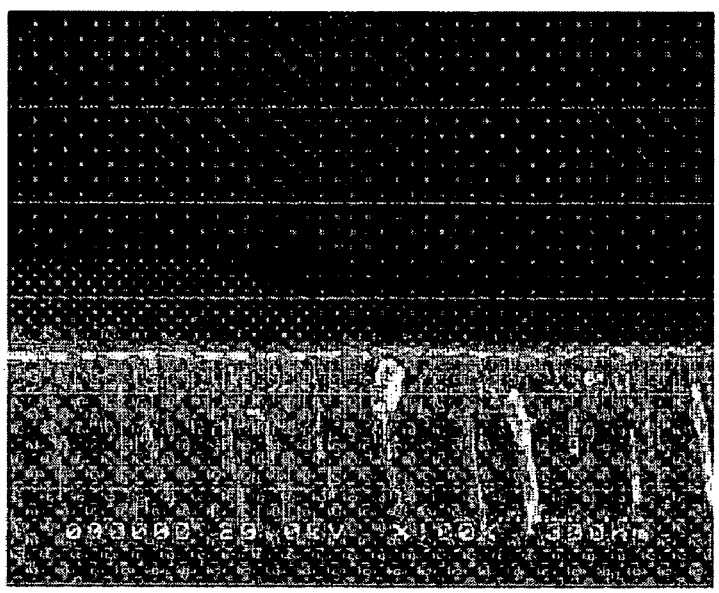
FIGS. 7A and 7B are SEM images of a layer formed using a conventional Ge precursor and a layer formed using a Ge precursor according to an embodiment of the present invention at 250°, respectively.
Figure 7B:
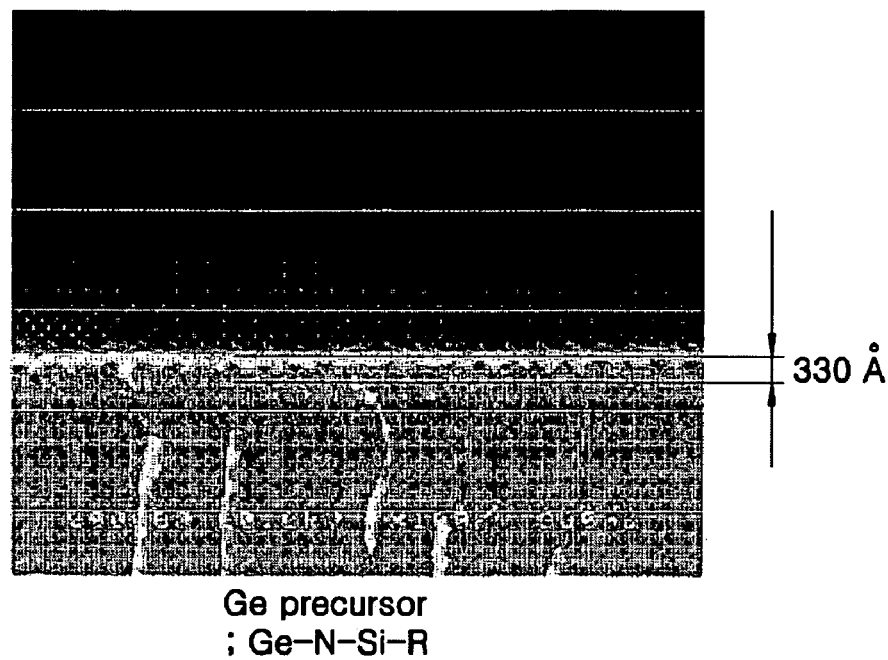

First, under deposition conditions shown in Table 1 below, a Ge thin layer was formed by ALD using Ge precursor A. Separately, a Ge thin layer doped with N and Si was formed using the Ge precursor 1 under the conditions and the method described above. Then, SEM images of cross sections of the two Ge thin layers were taken. The results are shown in FIGS. 7A and 7B. In particular, $H_2$ was used as shown in Table 1.

TABLE 1

| | |
|---|---|
| Deposition Temperature | 250° C. |
| Deposition Cycle | 250 times |
| Processing Period | 0.006/3/1/1 |
| Ar influx | 500 sccm |
| $H_2$ influx | 300 sccm |

Referring to FIG. 7A, forming a Ge thin layer was not properly achieved because the deposition temperature is low, such as 250° C. shown in Table 1. Referring to FIG. 7B, the Ge thin layer formed from the Ge precursor 1 was formed to a thickness of about 330 Å and was uniform (see the portion defined by two parallel lines in FIG. 7B). Thus, it was confirmed that Ge precursor 1 has an excellent layer-forming ability at a low temperature of about 250° C.

MEASUREMENT EXAMPLE 3

Pattern Forming Ability of Ge Precursor 1 at Low Temperature

Figure 8:
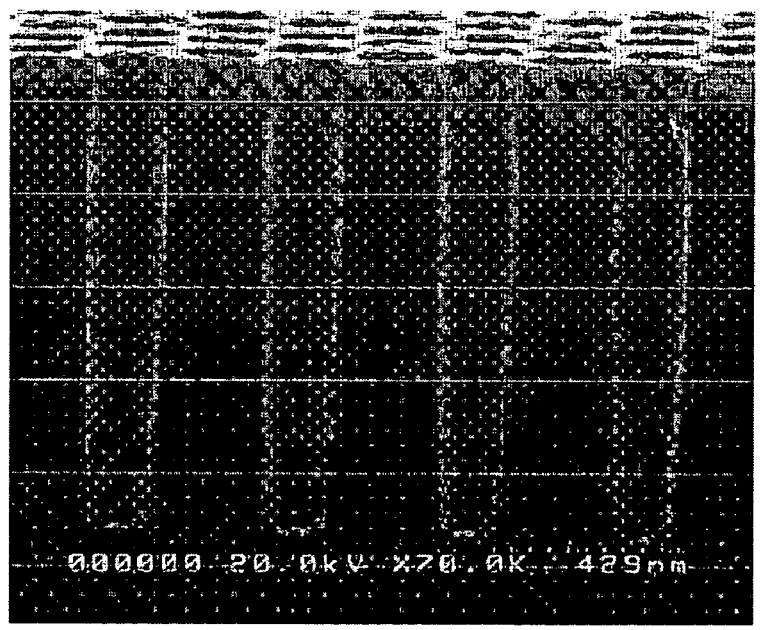
FIG. 8 is a SEM image of a pattern formed by depositing a Ge precursor according to an embodiment of the present invention at 250°.

The pattern forming ability of the Ge precursor 1 using ALD was measured. The results are shown in FIG. 8. More specifically, the Ge precursor was deposited on a silicon substrate having a plurality of trenches with a thickness of 18000 Å and a width of 960 Å under the deposition conditions indicated in Table 1. Referring to FIG. 8, the trenches, which are defined by white lines, were uniformly covered with a deposition of Ge precursor 1. Therefore, it was confirmed that Ge precursor 1 according to an embodiment of the present invention has an excellent pattern-forming ability.

MEASUREMENT EXAMPLE 4

Growth Rates of Ge Deposition Layer with Respect to Temperature

Figure 9:
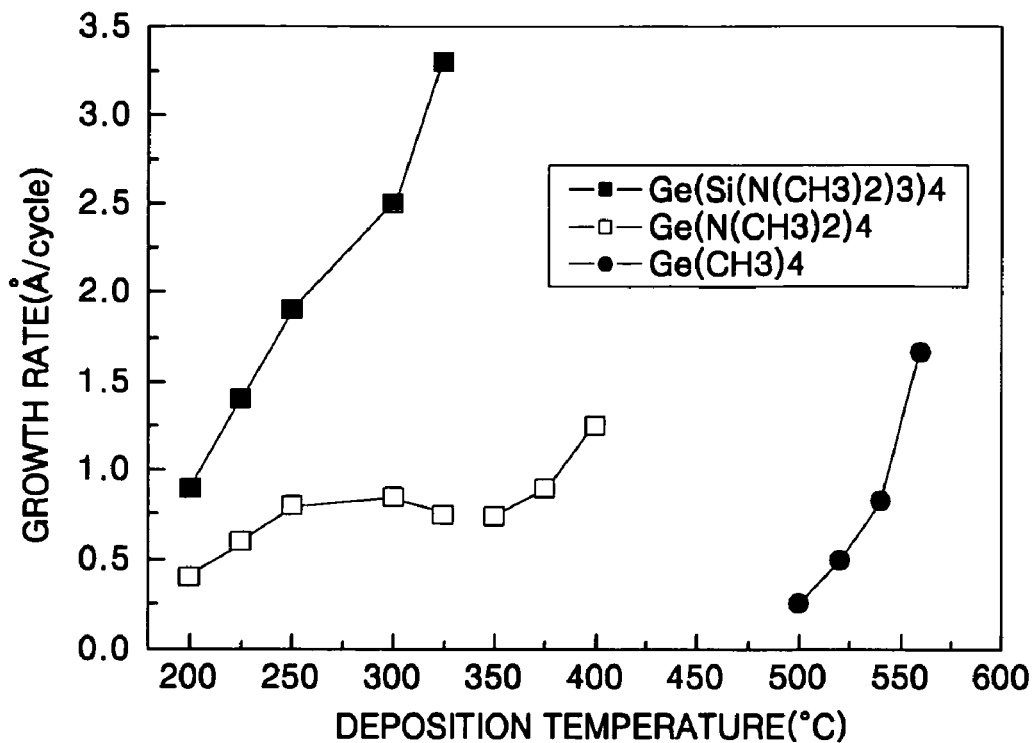
FIG. 9 is a graph of growth rate with respect to deposition temperature of the conventional Ge precursors and a Ge precursor according to an embodiment of the present invention.

Each of Ge precursors A, B, and 1 were deposited on a silicon substrate using ALD and the growth rate of each Ge deposition layer was measured. The results are shown in FIG. 9. The deposition conditions were those indicated in Table 1, except that the deposition temperature was varied. Each of the precursors A, B, and 1 was deposited at a temperature corresponding to scales in an x-axis representing temperature in FIG. 9.

Referring to FIG. 9, a layer from the Ge precursor A was not formed at a temperature less than 500° C., and a layer from the Ge precursor B exhibited a low maximum growth rate of about 1.2 Å/cycle at 200° C. to 400° C. That is, Ge precursor B was not suitable for obtaining a Ge thin layer with a predetermined thickness. On the other hand, at a low temperature of 200° C. to 350° C., the Ge precursor 1 was grown at a maximum growth rate of 3.2 Å/cycle, about three times faster than the Ge precursor B at the same deposition temperature. Therefore, it was confirmed that Ge precursor 1 according to an embodiment of the present invention is was suitable for a low temperature deposition process compared to conventional Ge precursors.

MANUFACTURING EXAMPLE

Formation of GST Layer and Measurement of the Resistance Thereof

Figure 10:
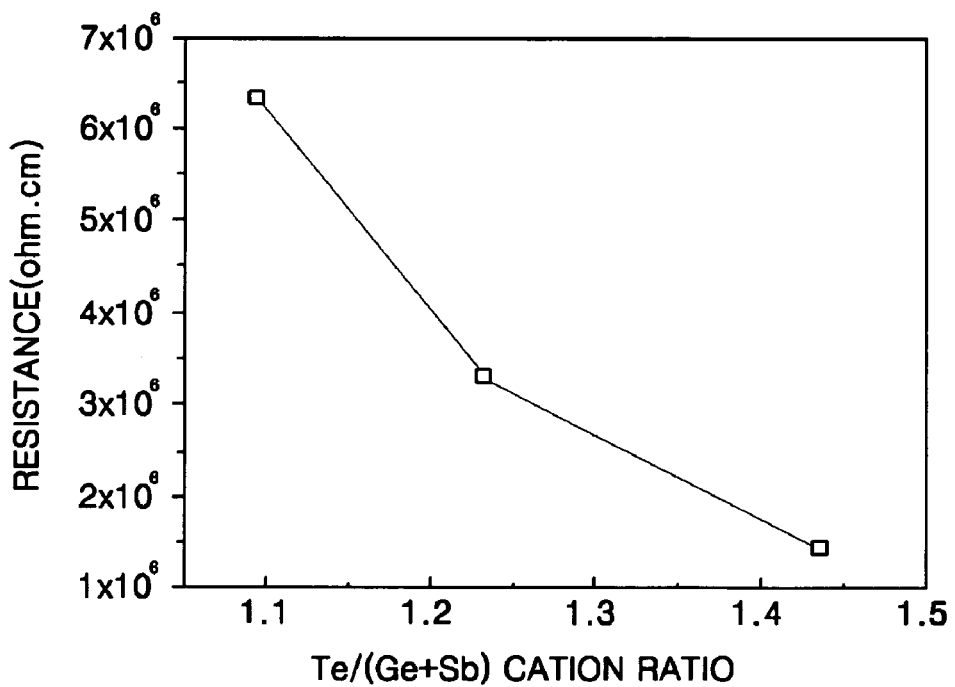
FIG. 10 is a graph of resistance with respect to Te(Ge+Sb) cation ratio of a GST layer doped with N and Si formed by depositing a Ge precursor according to an embodiment of the present invention, an Sb precursor, and a Te precursor.

Ge precursor 1, $Sb[(N(Si(CH_3)_3)_3]$ as an Sb precursor, and $Te[CH(CH_3)_2]$ as a Te precursor were deposited using ALD to form a $Ge_2Sb_2Te_5$ layer doped with N and Si. Except for the deposition temperature, the conditions during the ALD process were those indicated in Table 1. The temperature was controlled such that a Te/(Ge+Sb) cation ratio was about 1.1, about 1.25, and about 1.45, respectively. Then, the resistances of the produced GST thin layers doped with N and Si were measured. The results are shown in FIG. 10. Referring to FIG. 10, as the Te/(Ge+Sb) cation ratio increased, that is, the temperature increased, the resistance of the GST thin layer doped with N and Si decreased.

A Ge precursor for low temperature deposition according to the present invention contains N and Si such that the temperature at which the Ge precursor is deposited to form a thin layer, particularly, a GST thin layer doped with N and Si, can be low. The GST phase-change layer doped with N and Si formed from the Ge precursor for low temperature deposition has a low reset current. Therefore, a memory device including the GST phase-change layer doped with N and Si can be integrated, have a high capacity, and can be operated at a high rate.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A Ge precursor for low temperature deposition containing Ge, N, and Si, wherein the Ge precursor is represented by formula 1:

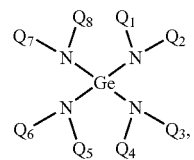

(1)

where $Q_1$, $Q_2$, $Q_3$, $Q_4$, $Q_5$, $Q_6$, $Q_7$, and $Q_8$ are each independently, H, a $C_{1-5}$ alkyl group, or $SiR_1R_2R_3$ and $R_1$, $R_2$ and $R_3$ are each independently, H or a $C_{1-5}$ alkyl group, provided that at least one group selected from the group consisting of $Q_1$, $Q_2$, $Q_3$, $Q_4$, $Q_5$, $Q_6$, $Q_7$ and $Q_8$ is $SiR_1R_2R_3$.

2. The Ge precursor of claim 1 represented by formula 2:

$$Ge[N(SiR_1R_2R_3)_2]_4 \qquad (2),$$

where $R_1$, $R_2$ and $R_3$ are each independently H or a $C_{1-5}$ alkyl group.

3. The Ge precursor of claim 1 represented by formula 3:

$$Ge[N(Si(CH_3)_3)_2]_4 \qquad (3)$$

4. A method of manufacturing a GST thin layer doped with N and Si comprising depositing the Ge precursor for low temperature deposition of claim 1, an Sb precursor, and a Te precursor at a deposition temperature equal to or less than about 350° C.

5. The method of claim 4, wherein the deposition temperature is in a range of about 200° C. to about 350° C.

6. The method of claim 4, wherein the Ge precursor for low temperature deposition, the Sb precursor, and the Te precursor are deposited using CVD or ALD.

7. The method of claim 4, wherein the Ge precursor for low temperature deposition, the Sb precursor, and the Te precursor are deposited using PEALD in which $H_2$ plasma is used.

8. A method of manufacturing a GST thin layer doped with N and Si comprising depositing the Ge precursor for low temperature deposition of claim 2, an Sb precursor, and a Te precursor at a deposition temperature equal to or less than about 350° C.

9. A method of manufacturing a GST thin layer doped with N and Si comprising depositing the Ge precursor for low temperature deposition of claim 3, an Sb precursor, and a Te precursor at a deposition temperature equal to or less than about 350°C.

* * * * *